(12) United States Patent
Duke

(10) Patent No.: US 6,974,075 B1
(45) Date of Patent: Dec. 13, 2005

(54) METHOD OF CONTROLLING A PERSON'S WEIGHT

(76) Inventor: Peter S. Duke, Mount Pleasant, Stoney Road, Kilcot, Newent, Gloucester (GB)

( * ) Notice: Subject to any disclaimer, the term of this patent is extended or adjusted under 35 U.S.C. 154(b) by 65 days.

(21) Appl. No.: 10/687,087

(22) Filed: Oct. 17, 2003

(51) Int. Cl.[7] .............................................. G06G 1/02
(52) U.S. Cl. ................... 235/375; 235/61 R; 235/375; 235/376; 235/87 A
(58) Field of Search ........................... 235/87 A, 61 R, 235/376, 375; 705/2–4, 7

(56) References Cited

U.S. PATENT DOCUMENTS

| | | | |
|---|---|---|---|
| 4,509,608 A * | 4/1985 | Hikita ............................ | 177/1 |
| 4,599,508 A * | 7/1986 | Smetaniuk ................... | 235/116 |
| D299,702 S | 2/1989 | Heim | |
| 5,785,650 A | 7/1998 | Akasaka et al. | |
| 5,873,369 A | 2/1999 | Lanaido et al. | |
| 5,902,234 A | 5/1999 | Webb | |
| 6,063,036 A | 5/2000 | Li | |
| 6,240,393 B1 * | 5/2001 | Brown ........................... | 705/1 |
| 6,605,038 B1 * | 8/2003 | Teller et al. ................. | 600/300 |
| 6,811,516 B1 * | 11/2004 | Dugan ............................ | 482/8 |
| 2003/0187683 A1 * | 10/2003 | Kirchhoff et al. .............. | 705/1 |

* cited by examiner

*Primary Examiner*—Ahshik Kim
(74) *Attorney, Agent, or Firm*—Donald R. Schoonover

(57) ABSTRACT

A slimming club is simulated so a person can visit a virtual slimming club via the Internet and can have his or her weight-related data reviewed automatically by a central computer system and will receive communication via any convenient method, including the Internet, telephone, fax, and other communication channels.

6 Claims, 1 Drawing Sheet

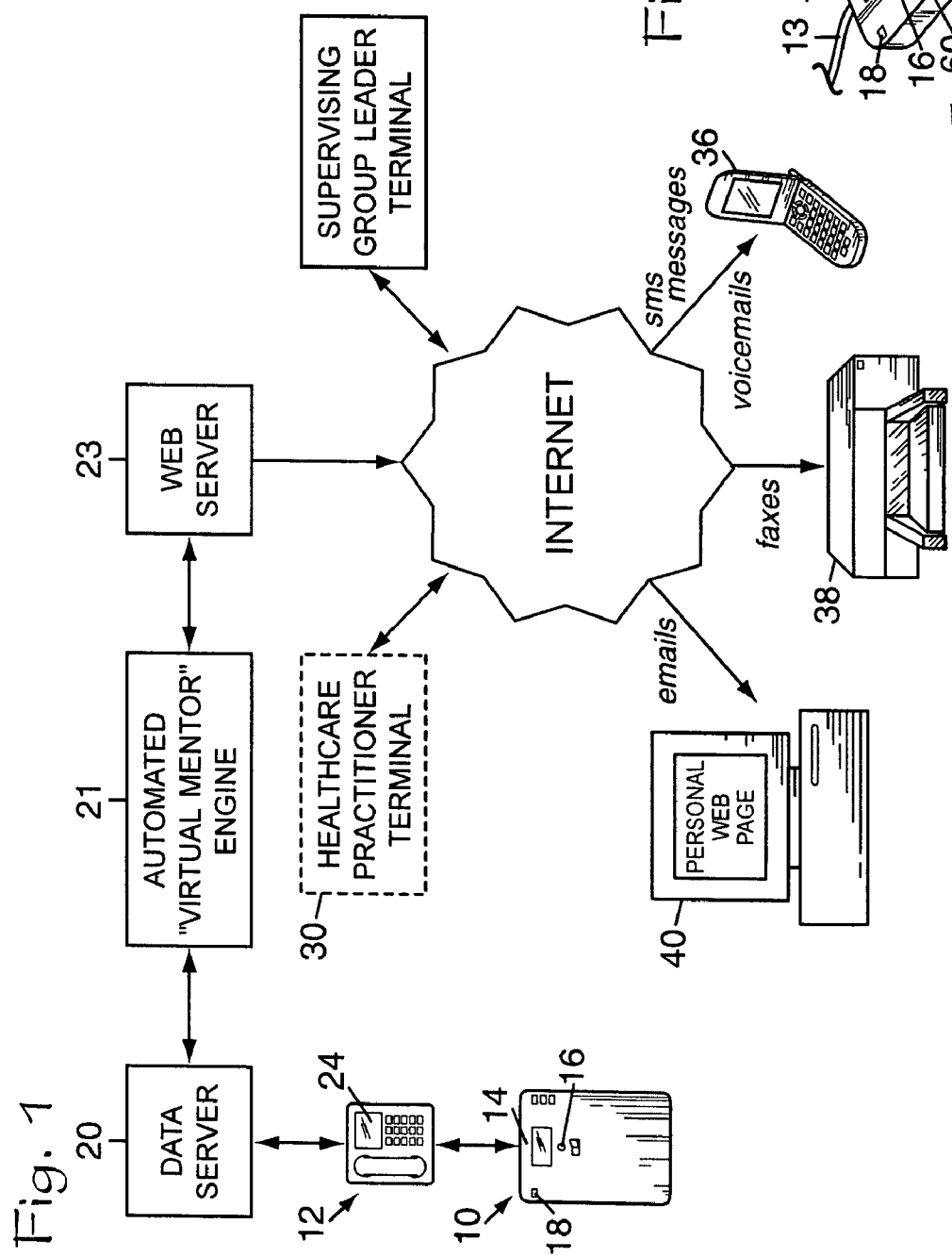
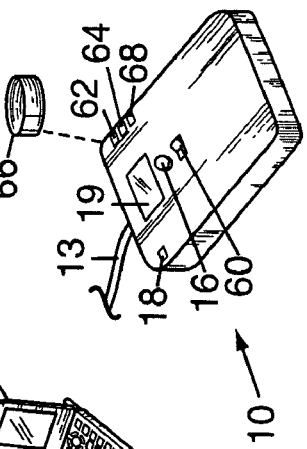
Fig. 1
Fig. 2

METHOD OF CONTROLLING A PERSON'S WEIGHT

BACKGROUND OF THE INVENTION

1. Field of the Invention

The present invention relates to the general art of weight control, and to the particular field of methods for effecting weight control.

2. Discussion of the Related Art

Many people are not at the weight that they desire and would like to lose weight or gain weight to achieve a weight that is either ideal or desired. However, the difficulties of changing one's weight have been well documented and many, if not most, people never achieve their goal.

Therefore, there is a need for an effective method for controlling a person's weight.

For this reason, the art contains a multiplicity of weight-control means and methods. These means and methods range from word of mouth to scientific. There are also a multitude of reasons why a particular means or method will not work or has not worked for each person. Some of these reasons include time, will power, monitoring, lack of positive reinforcement, lack of the proper reinforcement, and the like. For whatever reason, many of the prior art means and methods have failed to achieve maximum effectiveness.

One effective method for controlling a person's weight has been a personal program under the direction of a health care practitioner. One problem with this method is the time required for the person to travel to the location of the health care practitioner, and to be monitored and advised. This problem is often exacerbated if the person has to travel a sizeable distance to the health care practitioner. This problem often discourages a person from visiting the health care practitioner when he or she most needs to see that practitioner. Once a person begins to skip visits to the health care practitioner, that person often loses interest in the entire program.

Sometimes, it is not convenient for the person to travel to the health care practitioner who is monitoring and mentoring him. Sometimes, it is not convenient for the health care practitioner to see the person, and an appointment must be made. All of this may combine to discourage a person from remaining on a weight-control program.

However, the inventor has found that slimming clubs are a very effective method for losing weight. A slimming club normally consists of weekly group sessions supervised by a qualified group leader. A group leader is not necessarily a qualified health practitioner but is often a previous slimming club member who has successfully lost weight and kept his or her weight at a desired goal. These role model individuals are then trained by the slimming club to be able to supervise and conduct group sessions. These sessions typically last one to two hours. At these sessions, each member has his or her weight checked and recorded, called a "weekly weigh-in," and the member may stay as long or as little as he likes. Some members like to stay and discuss his or her progress, others just weigh in and leave. Those that have lost weight receive praise, often in a group setting, and those that have not lost weight receive encouragement and support. Those that just weigh in and leave because they cannot afford the time or for whatever reason are often those that struggle most with losing weight. One problem with this method is the time required for the person to travel to the location of the slimming club, and to be monitored and advised. This problem is often exacerbated if the person has to travel a sizable distance to the slimming club.

The key success ingredients in being a successful member of a slimming club are (i) regular, generally weekly, weigh-ins; and (ii) words or gestures of encouragement from the slimming club leader, such as notes through the mail, at a weekly meeting, or at random periodic intervals that are tailored to the needs of the individual.

Therefore, there is a need for an effective method for controlling weight which can include principles associated with slimming clubs but which is not subject to many of the drawbacks associated with slimming clubs.

PRINCIPAL OBJECTS OF THE INVENTION

It is a main object of the present invention to provide an effective method for controlling weight.

It is another object of the present invention to provide an effective method for controlling weight which can include principles associated with slimming clubs but which is not subject to many of the drawbacks associated with slimming clubs.

SUMMARY OF THE INVENTION

These, and other, objects are achieved by a method of controlling a person's weight which comprises simulating membership in a slimming club for the person by placing a weight-related reading device in a location that is convenient to the person, such as in the person's home, generating weight-related data signals from the weight-related reading device, providing a central computer system remote from the location of the data reading device, using a telephone connection to connect the weight-related reading device to the central computer system, receiving the weight-related data signals at the central computer system, and storing information associated with the person at the central computer system; and further simulating membership in a slimming club for the person by generating a reply communications signal from the central computer system every time a weight-related data signal is received at the central computer system from the weight-related reading, providing a communications signal receiving device for the person, using the communications signal receiving device, receiving the reply communication signal from the central computer system, forming a reminder communications signal at the central computer system, if a signal from the weight-related reading device has not been received at the central computer system in a predetermined time interval, generating the reminder communications signal from the central computer system, and using the communications signal receiving device, receiving the reminder communication signal from the central computer system.

The method embodying the present invention is thus able to simulate a slimming club membership for a person and will provide the advantages associated with slimming clubs while permitting the person to remain at home or at some other convenient location. The person need not travel to the location of the slimming club associated with the program. Messages and queries from the person are also convenient since they can be sent to the supervising group leader whenever the person has a question or a comment and the supervising group leader can review and reply at his or her convenience. The supervising group leader can review the data associated with the person at any time and then can communicate with that person when it is most convenient to the group leader. The person can review the communication from the central computer system and/or the supervising group leader when it is convenient to do so. Furthermore, some of the communication from the supervising group leader can be automated (such as a reminder to check in, or the like).

A virtual slimming club is thus created by the means and method of the present invention.

BRIEF DESCRIPTION OF THE DRAWING FIGURES

FIG. 1 is a schematic showing the overall system and indicating the method embodying the present invention.

FIG. 2 is a perspective view of a weight-related data gathering device, such as an electronic scale, used in the method embodying the present invention.

DETAILED DESCRIPTION OF THE PREFERRED EMBODIMENT

Other objects, features and advantages of the invention will become apparent from a consideration of the following detailed description and the accompanying drawings.

In a slimming club like any organization, there are good group leaders and bad group leaders. In between the group sessions, the most effective group leaders find creative and multiple ways of passing encouragement on to the members of their group. This can be in the form of telephone calls, short personal notes through the mail, and/or by email. This can be linked to extra encouragement around events likely to cause "slip-ups" in their progress, like birthdays or other special events where their will power is tested. The more encouragement the person receives, the higher are the chances for them to successfully lose weight.

The concept behind the present invention is to capture the behavior of the most effective group leaders and simulate this environment in a virtual slimming club but without the necessity of actually attending a group. When subscribing to the virtual club, the user will be assigned a group leader, i.e., the name of a person but all interactions with this virtual group leader will be automatically created by the system of the present invention including pre-recorded audio. It will be possible to have dialog with a real group leader but only on an infrequent basis. All other stimuli is automatically created by the system of the present invention, which uses a large variety of mechanisms, such as emails, faxes, text messages to mobile phones, letters, notes, birthday cards, digital TV, etc. In other words, the concept of the present invention is to present a user with as much encouragement stimuli through as many different means as reasonably possible.

The concept of this invention is to provide a system that uses technology to simulate membership of a slimming club but in a fully automated manner and administered to individual's in their homes.

A person wishing to subscribe to the virtual slimming club of the present invention will be provided with a special set of bathroom scales and a password for use on an Internet site. The Internet site and the scales effectively work independently.

A new subscriber records certain data in a central computer system in order for the automatic mentoring processes to bethereof activated. Such recording is accomplished by logging onto a computer system through the Internet to a secure personal web page. The subscriber is prompted to provide pre-determined specific details including his or her current weight; current Body Fat Index; weight goals, i.e., desired weight loss per week; desired weigh-in frequency; demographic data; personal data; family data; family birthday dates; vacation dates; etc. Multiple contact mechanisms, including email, cellular phone, voicemail, fax, digital TV, regular phone number, etc., but no external human intervention, is permitted during this procedure. The new subscriber must determine and set his or her own weight loss goals although the system of the present invention provides recommended goals and on-screen suggestions through the Internet site. A user is also prompted to enter a unique 10-digit identifier number that is supplied by their data acquisition device, or special bathroom scale, as described hereinbelow. The unique 10-digit identifier number is provided on a pre-printed label attached to the bottom of the special bathroom scale. All of the subscriber's data is recorded in a Subsciber Profile Database. Upon successful completion of entering the profile data, the subscriber is informed, both at that time and by subsequent email, of the personal name of their assigned slimming club group leader.

The data acquisition device consists of a digital electronic bathroom scale manufactured in plastic, metal and electronic components. There are two versions of the scale: (i) weight only, and (ii) weight plus Body Fat Index (BFI). In both versions, the scale has an inbuilt electronic modem dialer, a send button on the top of the scale, and a small LCD message window. The scale is connected to a regular home telephone line or cable. All electronic processes are controlled by a master control integrated circuit board. The scales are battery operated and include a battery compartment located on the underside of the scale.

Each scale contains a memory chip that holds a pair of pre-programmed unique 10-digit identifier numbers to enable the scale to be used by a maximum of two different users. Each user is simply identified on the scale display either as "User A" or "User B." A physical metal or plastic sliding switch allows users to switch between User A and User B. The scale has an on-board electronic memory that stores the last weight recording for each user. The scale compares the current weight of a user with the previously recorded weight; if the comparison differs by more than 5% of the stored value, the scale automatically determines that a different user (e.g., User A instead of User B) may be using the scale. In response thereto, the scale prompts the current user to confirm that he or she is the person associated with the user identifier (i.e., User A or User B) by pressing a button. No data entry other than pressing the button is needed to accomplish this process. In this manner, costs are minimized as no data input device is needed on the scale particularly since a single set of scales can only be used by two different members.

In an application of the present invention, a user simply stands on the scales whereupon weight and BFI are calculated and displayed. BFI is determined by using body resistance methods taken through foot pad electrodes on the surface of the scale. This technique is readily available in many commercially produced bathroom scales. If the user wishes to transmit his or her data to the central computer system, a simple press of a send button activates the modem dialer and sends the data to a central data server through a connected phone line or cable. The data being transmitted consists of the recorded weight, BFI and the unique identifier. Simple fault LCD messages may be displayed on the scales, such as "No dial tone," "phone line busy," "server busy," "server not responding," etc. If the data is received by the central data server, a confirming message is displayed on the scales. Thereupon, the telephone connection is terminated and the user may disconnect the cable or telephone line from the scales if desired. In other words, it is simply the action of standing on the scales and pressing the send button that activates the scales to send the necessary data. No separate connection such as through other in-house equipment is required.

A user may transmit the data as often or as infrequent as he or she wishes although, preferably, the user would follow the pre-selected weigh-in frequency. The data received by the central data server is recorded in a central weight database wherein a record is created for each unique identifier number and each transmission of weight/BFI data is recorded under that unique identifier together with date/time of data receipt. This database contains no other data and no means of knowing or associating this data with the actual identity of the person using the scales; it is simply a database of records of successfully submitted time/date stamped, weight/BMI data for a unique 10-digit identifier number obtained from within the corresponding scales. By maintaining the weight data stored in such an anonymous manner prevents unauthorized access to personal data.

The scales can be used in the subscribers home or taken wherever there is access to a telephone connection, e.g., at the office, on vacation, etc., with the limitation that the scales can only be used by either one of the two subscribibg members associated with that set of scales. The scales only send data and have no means of receiving messages other than confirmation of successful data transfer. Therefore, the scales only need to be connected to a cable or phone line when it is required to send data. At all other times, the scales behave as and can be used as a normal bathroom-type scale.

Computer software of the present invention, sometimes referred to herein as an Automated Virtual Mentor Engine, resides on a network connected to the weight database data server and to a profile database and web server. The Automated Virtual Mentor Engine simulates the behaviour of a slimming club group leader without human intervention by applying rules that replicate how a real group leader would manage each club member. Each day the Automated Virtual Mentor Engine automatically reviews each subscriber record according to pre-determined rules. Each subscriber will have recorded in his or her subscriber profile data the unique digit identifier number for their scales. By using this unique identifier number, one of the daily routines of the Automated Virtual Mentor Engine is to see if a new weight recording has been received in the weight database for that number. If such a new weight recording has been received, then the production of a new weight loss progress chart is automatically triggered and sent by mail or email to the subscriber and also posted to their personal internet page. If the newly recorded weight indicates a loss according to plan, then the system of the present invention may generate a message similar to "well done, keep it up." Conversely, if the indicated weight loss is not according to plan, then a message similar to "don't give up, keep trying" would be created These messages can be in the format of emails, SMS text messages, SMS picture messages, faxes, computer generated voicemails, etc., that are forwarded to a variety of destination devices as requested by the subscriber as indicated in his or her profile. If there should have been a new weight recording according to the subscribers pre-selected weigh-in frequency and none are found on the weight database, then a reminder is automatically dispatched to the subscriber by email. In all cases the messages will appear to have originated from their denominated personal group leader.

In order to simulate the behavior of effective slimming club group leaders, the objective is to use multiple methods of stimulus including using the integration of personal information like birthdays, family birthdays, special occasions, vacations, etc. These times can be particularly difficult for maintaining a weight loss programm. This data is used to trigger messages of encouragement as well as make the subscriber feel that they are being cared for in a personal way. This could for example be a simple "Well Done" card though the mail when the subscriber has reached a certain milestone, or a Birthday Card containing a message similar to "Happy Birthday, Do not overdo it too much tonight if you are going out to celebrate !!". The messages would be "signed" as if they had come from an actual slimming club group leader and would be the named individual; in the case of computer generated voice messages the same pre-recorded voice for this named individual would always be used. In this manner, the subscriber feels cared for on a personal basis. The Automated Virtual Mentor Engine contains the rules and logic of how and when these messages are triggered with the rules not being subscriber specific.

The Automated Virtual Mentor Engine also contains rules that periodically trigger messages that are sent to one of several group leaders who are real people employed to provide some level of personal intervention and to respond to email requests for advice. These people are not necessarily physically located at the same location of the central system. These messages can be triggered when, for example, a subscriber's weight loss program is determined by the rules contained in the Automated Virtual Mentor Engine to be significantly off track, in which case the group leader is prompted to make a personal telephone call to the subscriber. Personal intervention from the small number of group leaders is minimal and occurs only when triggered by the Automated Virtual Mentor Engine, which contains the rules and logic of how and when these messages are to be triggered. However, each subscriber will receive at least one personal call from the group leader over the course of a year, as scheduled by the Automated Virtual Mentor Engine, to make them feel that the service is personal and real. In this manner, one group leader can generally manage several hundred, if not thousands, of subscribers.

Each subscriber also has access to a secure personal web page where he can modify his personal details and can view his historical events in a variety of formats. The subscriber can request advice by submitting questions through email or through his secure web page. In addition, the subscriber can request a personal consultation at an extra charge.

It is to be understood that the system of the present invention can also be applied in a health practitioner setting. The health practitioner can use the same solution via a health practitioner station to access weight related data and can either manage this data by individual and personal interaction with their patient and/or by utilizing any of the automated features of the virtual slimming club.

Referring to the Figures, it can be understood that the present invention is embodied in a method of controlling a person's weight. As will be discussed below, the method can also be used to control stress as well. However, in the interest of simplicity of discussion, the method will be disclosed in connection with weight control, it being understood that the method can also be used to monitor and control stress as well as will be understood by those skilled in the art based on the teaching of the present disclosure.

The weight control method of the present invention comprises providing an electronic weight-related data gathering and measuring device, such as an electronic scale 10 that can be located in any convenient location, such as in a person's home.

The method embodying the present invention includes simulating membership in a slimming club for the person and creating a virtual slimming club. The method comprises electrically connecting the electronic weight-related data gathering device to a telephone system 12 via landline cord 13. The telephone system can be a landline system or an over-the-air system. The electronic weight-related data gathering device is provided with a dialing modem 14. The electronic weight-related data gathering device is provided with a "send" circuit 16, and the dialing modem is programmed to dial a prescribed telephone number when the "send" circuit is activated.

The electronic weight-related data gathering device is provided with a weight-related data reading circuit 18, and weight-related data is selected from the group consisting of body weight and body fat. A weight-related data signal corresponding to a weight-related data signal from the electronic weight-related data gathering device is generated and sent via the telephone system when the "send" circuit is activated.

The method further includes displaying weight-related data of the electronic weight-related data gathering device on a screen 19.

A data server 20 is provided and connected to the electronic weight-related data gathering device to receive weight-related data signals from the electronic weight-related data gathering device.

The electronic weight-related data gathering device is logged onto the data server 20, and weight-related data signals from the electronic weight-related data gathering device are stored on a central database.

The method embodying the present invention further includes generating communication status signals on the electronic weight-related data gathering device which indicate whether a telephone connection has been made, if a telephone connection is possible, if weight-related data signals are sent, if a dial tone is sensed, if the telephone line is busy, if the data server is busy, if the data server is not responding and the like. Such signals are displayed on a screen, such as screen 24 or screen 19.

The method further includes providing a central computer system 20, 21, 23 and locating the central computer system remote from the electronic weight-related data gathering device.

The method further includes providing a health care practitioner station 30 (for use in a health practitioner setting only) and locating the health care practitioner station remote from the central computer system. The health care practitioner's station can be in a clinic, a hospital, a doctor's office, a clinicians's office or the like.

A unique identifier associated with the person is made and kept in the central computer system and the unique identifier is used to associate records and data with the person at the central computer system.

The central computer system is connected to the Internet, Thus, a single supervising group leader can service a multitude of users who can be located near and far from the group leader. The users and the group leader need not even be in the same state, or even in the same country for that matter. The only connection between the group leader and the users is the Internet and/or a telephone communications system.

The method of the present invention further includes, at the central computer system, steps of receiving weight-related data signals sent from the electronic weight-related data gathering device via telephone connection, via the personal web page 40 making a record of the person's weight in the central computer system, making and keeping a record of the person's weight goals in the central computer system, making and keeping a record of special dates, such as birthdays, anniversaries, or the like that may be times when eating may bear special vigilance, associated with the person in the central computer system, making and keeping a record of an initial weight associated with the person in the central computer system, making and keeping a record of body fat and body fat index associated with the person in the central computer system, making and keeping a record of current weight associated with the person in the central computer system, making and keeping a record of rate of weight loss associated with the person in the central computer system, making and keeping a record of desired weigh-in frequency associated with the person in the central computer system, making and keeping a record of family data associated with the person in the central computer system, making and keeping a record of contact data associated with the person in the central computer system, making and keeping a record of positive reinforcement messages associated with the person in the central computer system, making and keeping a record of demographic data associated with the person in the central computer system, making and keeping a record of vacations associated with the person in the central computer system, and making and keeping a record of holidays associated with the person in the central computer system. The method further includes at the central computer system, forming a reply communication signal that is associated with the person by combining the person's weight, the persons's weight goals, the person's special dates, the person's vacations, the person's holidays, the person's initial weight, the person's body fat, the person's body fat index, the person's rate of weight loss, the person's weigh-in frequency, the person's positive reinforcement messages, and the demographic data associated with the person. This reply can be in the form of a printout, or a graphical representation or the like.

The method embodying the present invention further includes further simulating a membership in a slimming club for the person by generating the reply communication signal from the central computer system every time a weight-related data signal is received at the central computer system from the electronic weight-related data gathering device, selecting a communications signal receiving device associated with the person from the group consisting of a telephone 36, digital television, a facsimile machine 38, a computer 40 or mail.

Using the communications signal receiving device, the reply communication signal from the central computer system is received.

If a weight-related data signal from the electronic weight-related data gathering device has not been received at the central computer system in a predetermined time interval, a reminder communications signal is formed in the central computer system in accordance with the records of the person's goals, special dates, weigh-in frequency, vacations, holidays, reinforcement messages, and rate of weight loss. The reminder signal can include a positive reinforcement message as well and can include a statement concerning a special date if applicable.

The reminder communications signal is generated from the central computer system, and using the communications signal receiving device, the reminder communication signal from the central computer system is received at the location of the electronic weight-related data gathering device, or any other location designated by the person. The reminder communications signal can be sent by means of a program that is controlled according to the person's goals, weigh-in frequency, special dates and the like. Thus, for example, if the person has not sent in data in more than five days, the reminder signal can be sent, or if it is near a person's birthday or other such date when the person is likely to over-eat, the reminder signal can be automatically generated.

The method of the present invention can also include a step of comparing the person's previous weight-related reading to a current weight-related reading and generating a compatibility signal when the current weight-related reading differs from the previous weight-related reading by more than a predetermined amount, such as, for example, five percent of the previous reading. The compatibility signal is formed within the electronic weight gathering device and a message asking the user to confirm their identity is displayed on screen 14 or 19 by a special program embedded in the weight-related data gathering unit. A simple switch, such as switch 60, can be placed on the weight-related data gathering unit, such as the electronic scale shown in FIG. 2. Other means and methods for identifying a particular user can be used as will occur to those skilled in the art based on the teaching of this disclosure.

Still further, the method embodying the present invention can include a step of generating a query message if no data has been received from the person in a predetermined time period. This time period can be set by the person, or can be formed using the person's goals, or the like, through consultation between the person and supervising group leader.

As mentioned above, the method embodying the present invention can also be used to monitor and mentor stress of a person. Stress can be measured using heart rate as measured by a circuit 62, together with beat-to-stress beat Heart Rate Variability (HRV) as measured by a electrocardiogram (ECG) circuit 64. Cuff electrodes, such as electrode 66, can be attached to the person and electrically connected to the electronic device sending signals to the central computer system. A timing mechanism 68, can also be included and can be set for five minutes or the like, to measure the signals required for the stress signals.

It is possible to calculate beat-to-stress beat HRV by taking and processing an electrocardiogram (ECG) signal from the foot pad electrodes on the weight data gathering device such as the electronic scale shown in FIG. 2, and via the cuff electrodes attached to the person's wrists. The electronic scale can also include the aforementioned timing mechanism set to five minutes after which the system resets and generates an error signal. After the preset interval the data is transmitted using the same mechanism. The data can include a unique reference number, the person's weight, BFI and beat-to beat HRV.

The software in the central computer system can include routines having the ability to calculate a stress index from the HRV data. This will be on a scale of 1 to 10. The scale indicates the body's stress reserve and is calculated using public domain algorithms for interpreting HRV and stress reserve. The data and commentary are presented the same way as discussed above with regard to weight and BPI data.

It is understood that while certain forms of the present invention have been illustrated and described herein, it is not to be limited to the specific forms or arrangements of parts described and shown.

What is claimed and desired to be covered by Letters Patent is as follows:

1. A method of controlling a person's weight comprising:
   a) providing an electronic weight-related data gathering device, such as an electronic scale, in a convenient location, such as in a person's home;
   b) simulating membership in a slimming club for the person by
      (1) electrically connecting the electronic weight-related data gathering device to a telephone system,
      (2) providing the electronic weight-related data gathering device with a dialing modem,
      (3) providing the electronic weight-related data gathering device with a "send" circuit,
      (4) programming the dialing modem to dial a prescribed telephone number when the "send" circuit is activated,
      (5) providing a weight-related data reading circuit in the electronic weight-related data gathering device,
      (6) selecting weight-related data from the group consisting of body weight and body fat index,
      (7) generating and sending a weight-related data signal corresponding to the weight-related data from the electronic weight-related data gathering device via the telephone system when the "send" circuit is activated,
      (8) displaying weight-related data on the electronic weight-related data gathering device,
      (9) providing a data server and connecting the data server to the electronic weight-related data gathering device to receive weight-related data signals from the electronic weight-related data gathering device,
      (10) logging the electronic weight-related data gathering device onto the data server,
      (11) sending weight-related data signals from the electronic weight-related data gathering device via the telephone connection to the data server,
      (12) generating communication status signals on the electronic weight-related data gathering device which indicate whether a telephone connection has been made, if a telephone connection is possible, if weight-related data signals are sent, if a dial tone is sensed, if telephone line is busy, if the data server is busy, if the data server is not responding,
      (13) providing a central computer system,
      (14) locating the central computer system remote from the person,
      (15) providing a supervising group leader terminal,
      (16) locating the supervising group leader terminal remote from the person,
      (17) making and keeping a unique identifier associated with the person at the central computer system and using the unique identifier to associate records and data with the person at the central computer system,
      (18) connecting the central computer system to the Internet,
      (19) at the central computer system, receiving weight-related data signals sent from the electronic weight-related data gathering device via telephone connection and making and keeping a record of this data on a database,
      (20) making a record of the person's weight in the central computer system,
      (21) making and keeping a record of the person's weight goals in the central computer system,
      (22) making and keeping a record of special dates associated with the person in the central computer system,
      (23) making and keeping a record of an initial weight associated with the person in the central computer system,

(24) making and keeping a record of body fat and body fat index associated with the person in the central computer system,

(25) making and keeping a record of current weight associated with the person in the central computer system,

(26) making and keeping a record of rate of weight loss associated with the person in the central computer system,

(27) making and keeping a record of desired weigh-in frequency associated with the person in the central computer system,

(28) making and keeping a record of family data associated with the person in the central computer system,

(29) making and keeping a record of contact data associated with the person in the central computer system,

(30) making and keeping a record of positive reinforcement messages associated with the person in the central computer system,

(31) making and keeping a record of demographic data associated with the person in the central computer system,

(32) making and keeping a record of vacations associated with the person in the central computer system,

(33) making and keeping a record of holidays associated with the person in the central computer system, and

(34) at the central computer system, forming a reply communication signal that is associated with the person by combining the person's weight, the persons's weight goals, the person's special dates, the person's vacations, the person's holidays, the person's initial weight, the person's body fat, the person's body fat index, the person's rate of weight loss, the person's weigh-in frequency, the person's positive reinforcement messages, and the demographic data associated with the person; and c) further simulating a membership in a slimming club for the person by (1) generating the reply communication signal from the central computer system every time a weight-related data signal is received at the central computer system from the electronic weight-related data gathering device, (2) selecting a communications signal receiving device associated with the person from the group consisting of a telephone, digital television, facsimile machine, a computer or mail, (3) using the communications signal receiving device, receiving the reply communication signal from the central computer system, (4) if a weight-related data signal from the electronic weight-related data gathering device has not been received at the central computer system in a predetermined time interval, forming a reminder communications signal in the central computer system in accordance with the records of the person's goals, special dates, weigh-in frequency, vacations, holidays, reinforcement messages, and rate of weight loss, (5) generating the reminder communications signal from the central computer system, and (6) using the communications signal receiving device, receiving the reminder communication signal from the central computer system.

2. The method as described in claim 1 further including a step of comparing the person's previous weight-related reading to a current weight-related reading and generating a compatibility signal within the electronic weight-related data gathering device when the current weight-related reading differs from the previous weight-related reading by more than a predetermined amount.

3. The method as described in claim 2 further including a step of displaying a message on the electronic weight-related data gathering device requesting the user to confirm his/her identity.

4. The method as described in claim 1 further including monitoring stress level-related data on the person.

5. The method as described in claim 4 wherein the stress level-related data includes heart rate.

6. The method as described in claim 4 wherein the stress level-related data includes electrocardiogram (ECG) data.

* * * * *